United States Patent
Kienzle et al.

(10) Patent No.: US 6,273,898 B1
(45) Date of Patent: Aug. 14, 2001

(54) CLIP APPLICATOR

(75) Inventors: Karl-Ernst Kienzle, Immendingen; Rupert Mayenberger, Rielasingen; Dieter Weisshaupt, Immendingen, all of (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/573,357

(22) Filed: May 17, 2000

Related U.S. Application Data

(62) Division of application No. PCT/EP98/07478, filed on Nov. 20, 1998.

(30) Foreign Application Priority Data

Nov. 26, 1997 (DE) .............................................. 197 52 332

(51) Int. Cl.[7] .................................................. A61B 17/04
(52) U.S. Cl. .......................................... 606/142; 606/143
(58) Field of Search .................................... 606/142, 143; 227/175–180

(56) References Cited

U.S. PATENT DOCUMENTS

| | | | |
|---|---|---|---|
| Re. 35,525 | * 6/1997 | Stefanchik et al. | 606/142 |
| Re. 36,720 | * 5/2000 | Green et al. | 606/151 |
| 4,576,165 | 3/1986 | Green et al. | 606/143 |
| 4,637,395 | 1/1987 | Caspar et al. | 606/143 |
| 4,854,317 | * 8/1989 | Braun | 606/143 |
| 5,643,291 | 7/1997 | Pier et al. | 606/143 |
| 5,665,097 | * 9/1997 | Baker et al. | 606/143 |
| 5,843,097 | * 12/1998 | Mayenberger et al. | 606/143 |

FOREIGN PATENT DOCUMENTS

| | | |
|---|---|---|
| 33 35 986 | 4/1984 | (DE) . |
| 0 621 006 A1 | 10/1994 | (EP) . |
| 95/23557 | 9/1995 | (WO) . |
| WO 96/32891 | 10/1996 | (WO) . |

* cited by examiner

*Primary Examiner*—Gary Jackson
(74) *Attorney, Agent, or Firm*—Barry R. Lipsitz

(57) ABSTRACT

In a clip applicator having a handle, a magazine mountable on the handle and containing a number of clips, and a movable actuating grip on the handle, which is in direct or indirect engagement with a clip advancing device in the magazine when the magazine is mounted on the handle, to ensure that the coupling between the actuating grip on the handle and the clip advancing device in the magazine is in any event successful when mounting the magazine, it is proposed that a locking device be arranged on the handle for locking when in a lock position the actuating grip in an engagement position in which the engagement with the clip advancing device is able to be made upon mounting the magazine and for releasing the actuating grip when in a release position.

12 Claims, 4 Drawing Sheets

CLIP APPLICATOR

This application is a continuation of international application number PCT/EP98/07478 filed on Nov. 20, 1998.

BACKGROUND OF THE INVENTION

The invention relates to a clip applicator having a handle, a magazine mountable on the handle and containing a number of clips, and a movable actuating grip on the handle, which is in direct or indirect engagement with a clip advancing device in the magazine when the magazine is mounted on the handle.

Clip applicators of this kind are used to apply elastically bendable clips of U-shaped cross section to suitable body parts, for example, to prevent hemorrhages in the region of the scalp. In the clip applicator, the clips are provided in a magazine in which there are a number of clips which are advanced stepwise in the magazine towards its open end by a suitable actuating mechanism. At the open end, there is an opening and applying device for opening the respective foremost clip, applying it at the desired place and then releasing it so that the clip is held at the point of application by the inherent elasticity of its arms.

It is known to design the magazines as independent constructional units which are mounted on a handle, as required, and are removed from it again when empty. The handle has actuating devices for actuating via a mechanical coupling advancing elements in the magazine, which, in turn, advance the clips in the magazine (WO96/32891).

When mounting the magazines on such handles, the problem arises that a mechanical coupling between the actuating grip of the handle, on the one hand, and the advancing mechanism in the magazine, on the other hand, is only possible in a certain position of the actuating grip. On the other hand, it is precisely when mounting the magazine that uncontrolled movement of the actuating grip to very different positions by the operator is likely to occur, and the magazine will then not be able to be put in place.

SUMMARY OF THE INVENTION

The object of the invention is to so design a generic clip applicator that the mechanical coupling of the actuating grip and the clip advancing device in the magazine can in any case take place when mounting the magazine on the handle.

This object is accomplished in a clip applicator of the kind described at the outset, in accordance with the invention, in that there is arranged on the handle a locking device for locking in a lock position the actuating grip in an engagement position in which the engagement with the clip advancing device is able to be made when mounting the magazine, and for releasing the actuating grip in a release position.

The provision of such a locking device enables fixing of the actuating grip in the only position in which the mechanical coupling with the clip advancing device of the magazine is possible, and it is thus ensured that the coupling can take place without any problem when mounting the magazine.

It is particularly advantageous for the actuating grip to be displaceable by an elastic force into the engagement position. In order to be able to displace the locking device into the lock position, it is then no longer necessary to first move the actuating grip to this engagement position. This movement is already brought about by the elastic force, and, therefore, the actuating grip is automatically located in the engagement position after release. The applying of the locking device ensures that this engagement position of the actuating grip is also maintained when an operator grasps the clip applicator while mounting the magazine and possibly exerts forces on the actuating grip.

The elastic force for moving the actuating grip to the engagement position can, for example, be generated by a spiral spring clamped between actuating grip and handle.

It is also particularly advantageous for the locking device to be actuatable by the mounted magazine such that it is permanently in the release position. The magazine thus unlocks the locking device once it is located in the mounted position and so the user can immediately use the applicator after the magazine has been mounted, without having to unlock the actuating grip beforehand.

In accordance with a particularly preferred embodiment, provision is made for the locking device to be movable against the action of an elastic force out of the lock position into the release position. Thus, while the magazine is mounted, the locking device permanently remains in the release position and is thus inoperative, but if the magazine is removed, locking will automatically occur as the locking device moves into the lock position under the action of the elastic force once the actuating grip is located in the engagement position.

In a preferred embodiment, provision may be made for the locking device to comprise a locking body which is pressed under the action of a spring against the actuating grip or a part displaceable by the latter and in the engagement position of the actuating grip moves into a recess of the actuating grip or behind an edge of the actuating grip.

Herein it is advantageous for the locking body in its lock position to project into the path of movement of the magazine when mounting it on the handle and for the magazine to have a contact surface which places itself against the projection of the locking body when mounting the magazine and moves the locking body into the release position. Thus, the movement of the magazine when mounting it is used to move the locking device into the inoperative release position, and the user does not have to carry out any separate action for the unlocking.

In particular, the locking body can be in the form of a stepped piston displaceable in the longitudinal direction, and the thicker portion thereof in the engagement position of the actuating grip dips into a recess of the actuating grip, whereas the thinner portion then protrudes from the handle.

The thinner portion of the stepped piston can extend through a longitudinal slot of the actuating grip so that the actuating grip remains movable although the locking body is extending through it.

It is expedient for the thicker portion of the stepped piston to be mounted and guided in a housing which receives a compression spring resting at its end face against the stepped piston.

The housing can be releasably held on the handle, in particular, by screwing in place.

The following description of preferred embodiments of the invention serves in conjunction with the drawings the purpose of further explanation.

DETAILED DESCRIPTION OF THE INVENTION

Figure 1:
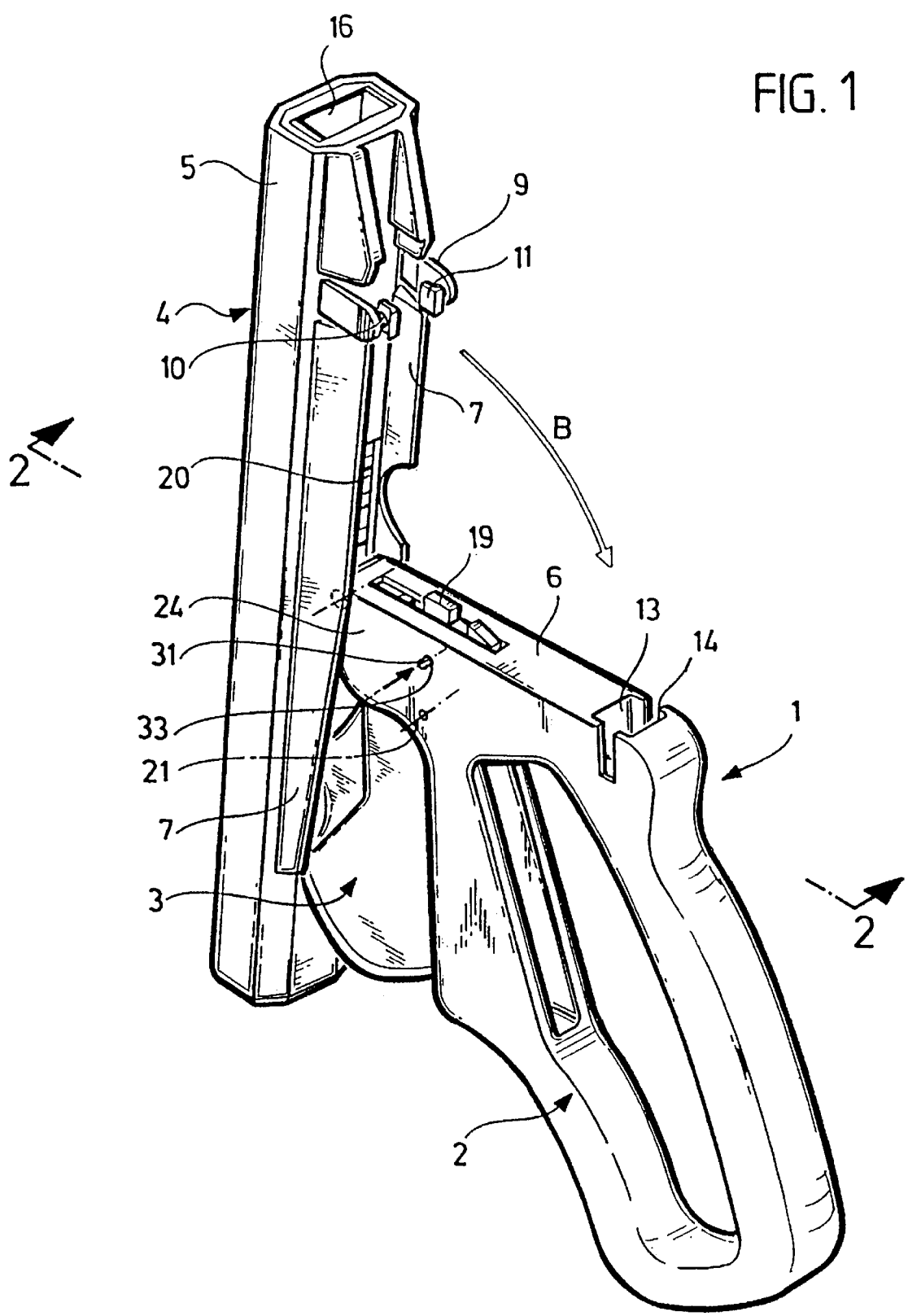
FIG. 1 a perspective view of a clip applicator while the magazine is being mounted.
Figure 2:
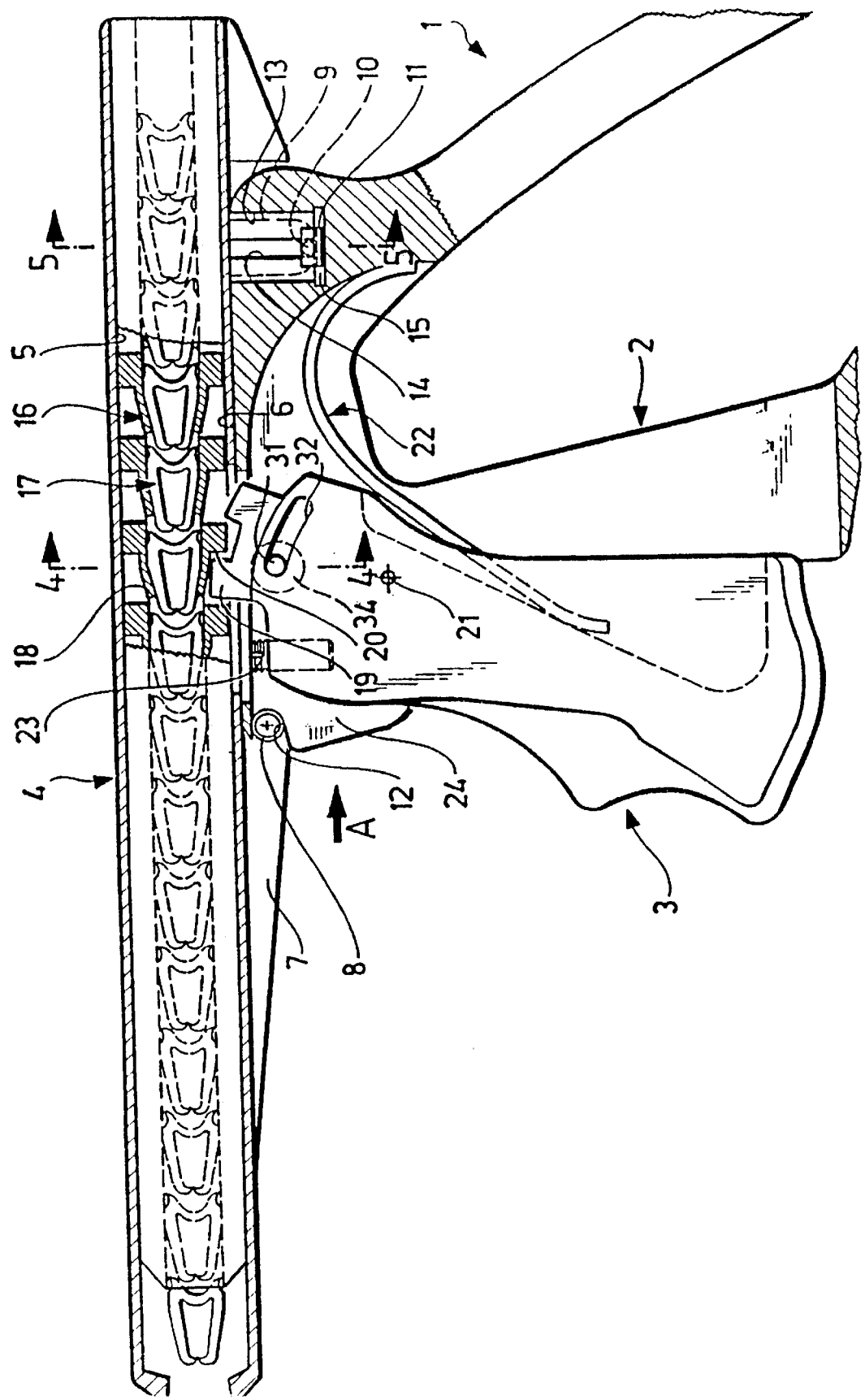
FIG. 2 a sectional view taken along line 2—2 in FIG. 1.
Figure 3:
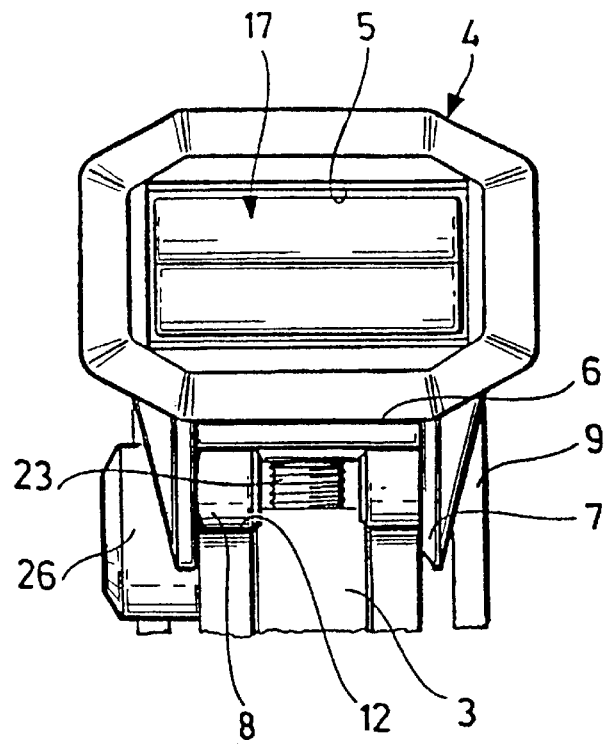
FIG. 3 a view of the clip applicator in the direction of arrow A in FIG. 2.
Figure 5:
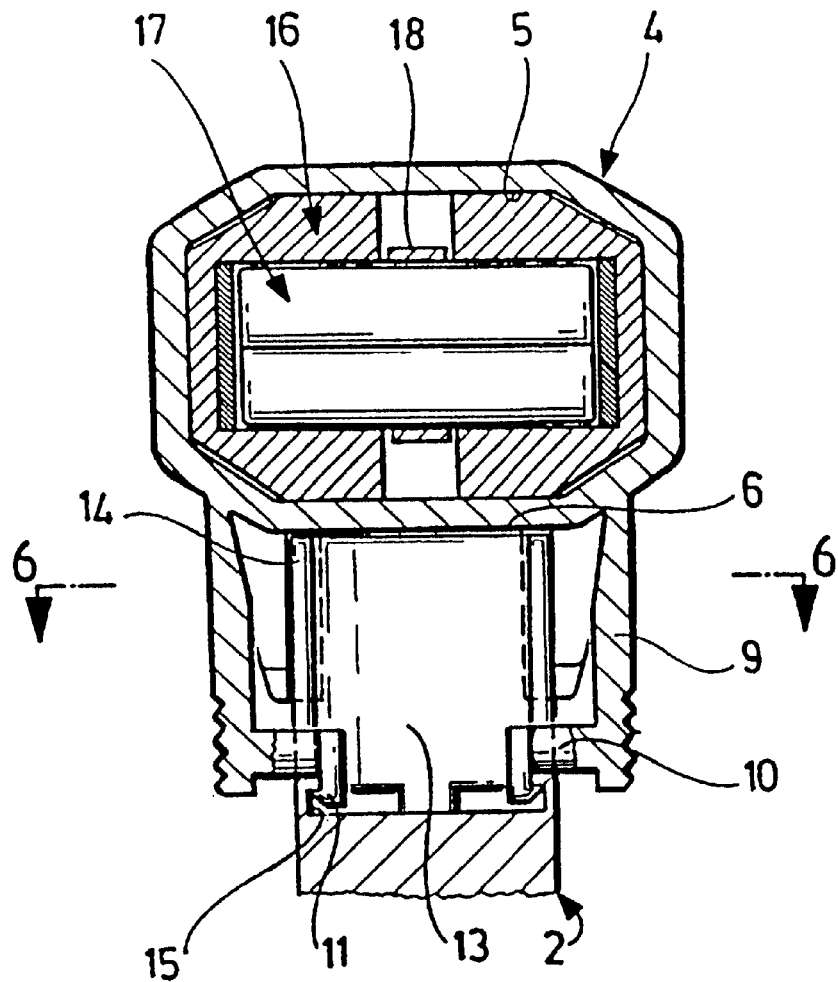
FIG. 5 a sectional view taken along line 5—5 in FIG. 2.
Figure 6:
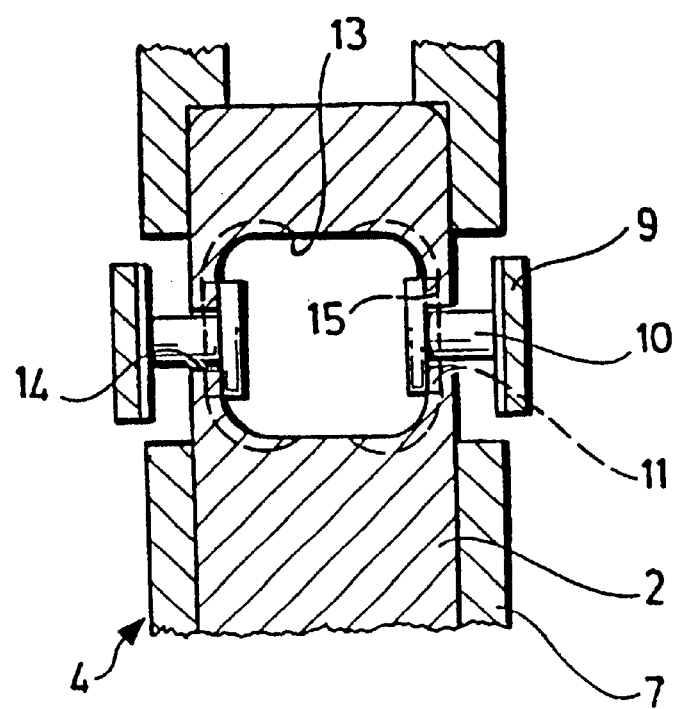
FIG. 6 a sectional view taken along line 6—6 in FIG. 5.

The clip applicator shown in the drawings comprises a pistol-shaped handle 1 with a stationary grip 2, an actuating grip 3 pivotably mounted on the handle 1, and a magazine 4 mountable on the handle 1. This magazine 4 comprises an elongate shaft 5 open at least at the front side and is positionable on an upper contact surface 6 of the handle 1 and lockable with the handle 1 in this position. For this purpose, the shaft 5 carries at two parallel, perpendicularly downwardly projecting wall portions 7 inwardly projecting bearing pins 8 and likewise downwardly projecting locking arms 9 which carry at their free ends inwardly projecting pins 10 with downwardly and outwardly pointing locking projections 11. The handle 1 comprises at the front side of the contact surface 6 U-shaped receptacles 12 which are open towards the front and into which the bearing pins 8 of the magazine 4 are insertable from the front so that a pivot axis is thereby formed for the magazine 4. In this position, the magazine 4 is pivotable in the direction of arrow B in FIG. 1 onto the contact surface 6, and the locking projections 11 of the magazine 4 then dip into an upwardly open locking aperture 13 at the rear end of the contact surface 6. The locking aperture 13 has at both of its sides vertical slots 14 through which the pins 10 can enter the locking aperture 13 from the outside, and the locking projections 11 engage behind recesses 15 at the lower end of the locking aperture 13 when the magazine 4 is fully positioned on the contact surface 6 (FIG. 5). The magazine 4 is thereby held on the handle 1, on the one hand, by the pins 10 engaging the receptacle 12, and, on the other hand, by the locking projections 11 engaging behind the recesses 15.

The locking arms 9 are elastically pivotable relative to each other by a pressure from the outside, which causes the locking projections 11 to be pushed out of the recesses 15, which, in turn, releases the magazine 4, which can then be pivoted in the direction opposite to the pivoting direction of arrow B and removed from the handle 1.

There is mounted for longitudinal displacement in the interior of the magazine 4 a channel-shaped housing 16 which accommodates in its interior a number of clips 17 of the same kind which are arranged one behind the other. The clips 17 are mounted in the interior of the housing 16 for displacement in the longitudinal direction, but are prevented by retaining elements engaging the sides of the clips from being pushed in the housing 16 towards its rear end. These retaining elements can, for example, comprise spring tongues projecting elastically into the interior of the housing 16, which are not separately shown in the drawings.

Also formed on the upper side and the underside of the housing 16 are spring tongues 18 which likewise extend forwards at an incline into the interior of the housing 16, approximately at the spacing of the clips 17 held in the housing 16. These spring tongues 18 can rest against the rear side of the clips 17 and thus push the clips 17 forwards together with the housing 16 when the housing 16 is advanced in the magazine 4. However, when the housing 16 is subsequently retracted again, the clips 17 remain in the advanced position owing to the retaining elements, and, therefore, during a subsequent advancing movement of the housing 16, the clips are again pushed forwards by the path of advance of the housing. By alternate advancing and retracting of the housing 16, it is thus possible to move the clips 17 in the interior of the magazine stepwise towards its open end.

In order to bring about such a reciprocating displacement of the housing 16 in the magazine 4, a driver 19 which is joined to the actuating grip 3 and projects upwards above the contact surface 6 engages in an opening 20 on the underside of the housing 16. Since the pivot axis 21 of the actuating grip 3 is arranged at some distance below the contact surface 6, a pivoting of the actuating grip 3 leads to a displacement of the driver 19 in the longitudinal direction of the contact surface 6, and this longitudinal displacement is transmitted to the housing 16.

There is held on the grip 2 a spiral spring 22 which is supported at its free end on the actuating grip 3 and pivots it into a forward, outwardly pivoted position in which the driver 19 stands in a furthermost retracted position. This position will be referred to hereinbelow as engagement position. In this engagement position, the actuating grip 3 is pivoted by the spiral spring 22 against a stop which in the illustrated embodiment is in the form of a screw 23 and whose position is adjustable by tightening this screw to a greater or lesser extent. The adjustment occurs such that in the engagement position the driver 19 engages without any problem in the opening 20 of the housing 16 of a magazine 4 when this magazine 4 is mounted in the described manner on the handle 1. In any other position of the driver 19, the latter would strike the edges of the opening 20, but in the engagement position the driver 19 fits directly into the opening 20 of the magazine, which, by the way, is always delivered with the housing 16 in the same position in the magazine 4.

The grip 2 surrounds the actuating grip 3 in the area between the pivot axis 21 and the contact surface 6 on both sides thereof in the form of a side wall 24 resting against the actuating grip 3. One of the two side walls has a continuous threaded bore 25 into which a pot-shaped housing 26 is screwed. This housing 26 receives the thicker portion 27 of a stepped piston 28. This thicker portion 27 is mounted for longitudinal displacement in the housing 26 and is urged out of the housing 26 against the actuating grip 3 by a helical spring 29 which is supported, on the one hand, on the bottom 30 of the housing and, on the other hand, on the thicker portion 27 of the stepped piston 28.

A thinner, rod-shaped portion 31 joined to the thicker portion 27 extends through a longitudinal slot 32 in the actuating grip 3 and an opening 33 in the opposite side wall 24.

On the side facing the housing 26, the actuating grip 3 has a recess 34 which is in alignment with the housing 26 when the actuating grip 3 is in the engagement position. In this engagement position, the stepped piston 28 with the thicker portion 27 can engage under the action of the helical spring 29 in the recess 34 and thus locks the actuating grip 3 in the engagement position. When the thicker portion 27 of the stepped piston 28 enters the recess 34 in this way, the thinner portion 31 of the stepped piston 28 extends through the opening 33 and protrudes there to a slight extent.

Figure 4:
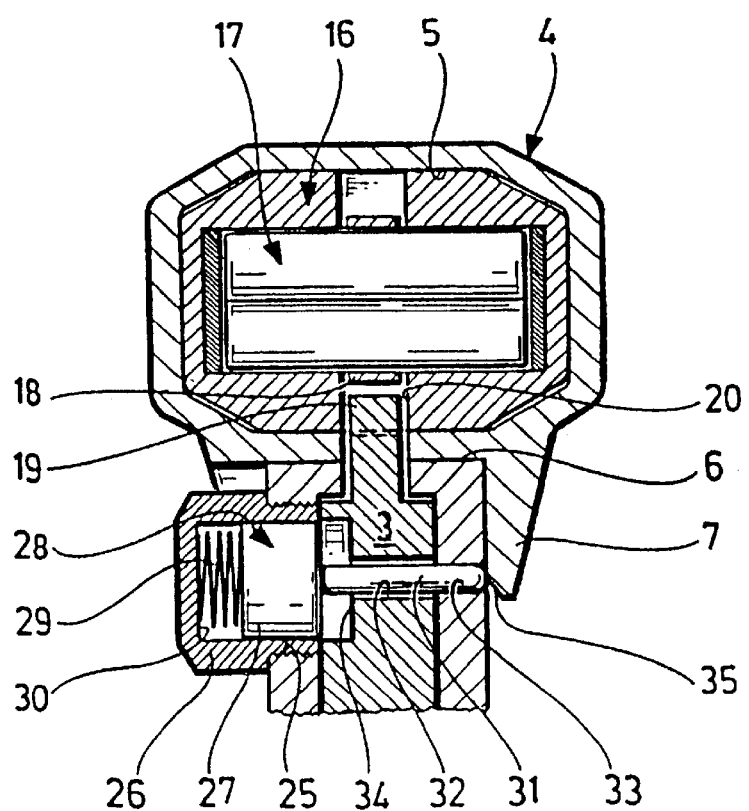
FIG. 4 a sectional view taken along line 4—4 in FIG. 2.

In the area immediately adjacent to the opening 33, the wall portion 7 of the magazine 4 is in the form of a slide surface 35 which comes to rest against the end of the thinner portion 31 of the stepped piston 28 protruding from the opening 33 when mounting the magazine 4 and pushes this thinner portion 31 into the opening 33 fully (FIG. 4) when the magazine 4 is fully mounted. The stepped piston 28 is thereby pushed into the housing 26 against the action of the helical spring 29 to such an extent that the thicker portion 27 of the stepped piston 28 emerges completely from the recess 34. In this position, the actuating grip 3 can be pivoted. Therefore, this position of the stepped piston 28 is referred to as release position, whereas the position in which the stepped piston 28 dips with its thicker portion 27 into the recess 34 is referred to as lock position because a pivoting of the actuating grip 3 is thereby prevented.

In the case of a handle 1 where a magazine 4 has not yet been mounted, the grip 2 is pivoted by the spiral spring 22 into the engagement position, and in this engagement position the helical spring 29 pushes the stepped piston 28 into the lock position since in the engagement position the recess 34 is in alignment with the housing 26. The actuating grip 3 is thus locked so as to prevent pivoting.

In the engagement position, it is located in this locked position and, therefore, when mounting the magazine 4 it is ensured that the driver 19 will be able to dip into the opening 20 provided therefor on the housing 16. During the last part of the mounting movement of the magazine 4, the slide surface 35 of the magazine places itself against the free end of the thinner portion 31 of the stepped piston 28 and thereby moves it into the release position so that after the mounting of the magazine 4, the clip applicator is unlocked and can be actuated in the desired manner.

Once the user removes the magazine again when it is empty, an automatic locking occurs as the grip 2 is pivoted by the spiral spring in the described manner into the engagement position and is locked there.

What is claimed is:

1. Clip applicator having a handle, a magazine mountable on said handle and containing a number of clips, and a movable actuating grip on said handle, said actuating grip being in direct or indirect engagement with a clip advancing device in said magazine when said magazine is mounted on said handle, characterized in that a locking device (28, 34) is arranged on said handle (1), and in a lock position said locking device locks said actuating grip (3) in an engagement position in which the engagement with said clip advancing device (16) is able to be made when mounting said magazine (4), and in a release position said locking device releases said actuating grip (3).

2. Clip applicator as defined in claim 1, characterized in that said actuating grip (3) is displaced into said engagement position by an elastic force.

3. Clip applicator as defined in claim 2, characterized in that said elastic force is generated by a spiral spring (22) clamped between actuating grip (3) and handle (1).

4. Clip applicator as defined in claim 1, characterized in that said locking device (28, 34) is actuatable by said mounted magazine (4) such that it is permanently located in release position.

5. Clip applicator as defined in claim 4, characterized in that said locking device (28, 34) is movable from the lock position to the release position against the action of an elastic force (29).

6. Clip applicator as defined in claim 1, characterized in that said locking device comprises a locking body (28) which under the action of a spring (29) is pressed against said actuating grip (3) or a part displaceable by said actuating grip, and in the engagement position of said actuating grip moves into a recess (34) of said actuating grip or behind an edge of said actuating grip.

7. Clip applicator as defined in claim 6, characterized in that in its lock position, said locking body (28) projects into the path of movement of said magazine (4) upon mounting on said handle (1), and in that said magazine (4) comprises a contact surface (35) which places itself against said locking body (28) when mounting said magazine (4) and thereby displaces said locking body into the release position.

8. Clip applicator as defined in claim 7, characterized in that said locking body is in the form of a stepped piston (28) displaceable in a longitudinal direction, and a thicker portion (27) of said stepped piston dips into said recess (34) of said actuating grip (3) in the engagement position of said actuating grip (3), whereas a thinner portion (31) then protrudes from a grip (2).

9. Clip applicator as defined in claim 8, characterized in that said thinner portion (31) of said stepped piston (28) extends through a longitudinal slot (32) of said actuating grip (3).

10. Clip applicator as defined in claim 8, characterized in that said thicker portion (27) of said stepped piston (28) is mounted and guided in a housing (26) accommodating a compression spring (29) which rests with its end face against said stepped piston (28).

11. Clip applicator as defined in claim 10, characterized in that said housing (26) is releasably held on said grip (2).

12. Clip applicator as defined in claim 11, characterized in that said housing (26) is screwed into said grip (2).

* * * * *

UNITED STATES PATENT AND TRADEMARK OFFICE
CERTIFICATE OF CORRECTION

PATENT NO. : 6,273,898 B1 Page 1 of 1
DATED : August 14, 2001
INVENTOR(S) : Kienzle et al.

It is certified that error appears in the above-identified patent and that said Letters Patent is hereby corrected as shown below:

<u>Title page,</u>
Item [62], Related U.S. Application Data, the word "division" is incorrect and [62] should read:

-- [62] Continuation of application No. PCT/EP98/07478, filed on Nov. 20, 1998. --

Signed and Sealed this

Twenty-sixth Day of November, 2002

*Attest:*

*Attesting Officer*

JAMES E. ROGAN
*Director of the United States Patent and Trademark Office*